United States Patent [19]

Frigerio et al.

[11] Patent Number: 5,075,324
[45] Date of Patent: Dec. 24, 1991

[54] ARALKYL-1,4-DIHYDROPYRIDINES, A METHOD FOR THEIR PREPARATION AND PHARMACEUTICAL COMPOSITION CONTAINING THEM

[75] Inventors: Marco Frigerio; Andrea Zaliani; Carmelo A. Gandolfi; Mauro Germini; Odoardo Tofanetti; Sergio Tognella, Milan, Italy

[73] Assignee: Boehringer Biochemia Robin S.p.A., Milan, Italy

[21] Appl. No.: 378,515

[22] PCT Filed: Dec. 21, 1987

[86] PCT No.: PCT/EP87/00815
§ 371 Date: Jun. 22, 1989
§ 102(e) Date: Jun. 22, 1989

[87] PCT Pub. No.: WO88/05043
PCT Pub. Date: Jul. 14, 1988

[30] Foreign Application Priority Data

Dec. 24, 1986 [IT] Italy .................. 22880 A/86
Sep. 4, 1987 [IT] Italy .................. 21796 A/87

[51] Int. Cl.$^5$ .......... C07D 211/90; C07D 401/06; A61K 31/455
[52] U.S. Cl. .................. 514/356; 514/79; 514/89; 514/222.2; 514/252; 514/259; 514/269; 514/307; 514/311; 514/332; 514/338; 514/340; 514/342; 514/343; 514/344; 514/352; 514/335; 544/3; 544/238; 544/244; 544/284; 544/333; 544/405; 546/22; 546/147; 546/148; 546/152; 546/263; 546/269; 546/271; 546/272; 546/273; 546/274; 546/275; 546/276; 546/280; 546/281; 546/286; 546/310; 546/318; 546/321; 546/322; 546/24; 546/261
[58] Field of Search .......... 546/22, 24, 261, 263, 546/284, 147, 148, 152, 269, 271, 272, 273, 274, 275, 276, 280, 281, 286, 310, 318, 321, 322; 514/335, 336, 344, 356, 79, 89, 222.2, 252, 259, 269, 307, 311, 332, 338, 340, 342, 343, 352; 544/3, 238, 244, 284, 333, 405

[56] References Cited

U.S. PATENT DOCUMENTS 4,338,322 7/1982 Sato .................. 514/356
4,492,703 1/1985 Goldmann et al. .......... 514/356
4,892,881 1/1990 Alker et al. .......... 514/356

FOREIGN PATENT DOCUMENTS 0172029 2/1986 European Pat. Off. .
5047656 9/1978 Japan .

OTHER PUBLICATIONS

Burger, A., Medical Chemistry, 2nd ed., Interscience, N.Y. (1960), pp. 565-571, 579-581 and 600-601.

Primary Examiner—David B. Springer
Assistant Examiner—Lenora Miltenberger
Attorney, Agent, or Firm—Armstrong, Nikaido, Marmelstein, Kubovcik & Murray

[57] ABSTRACT 1,4-dihydropyridines of formula I

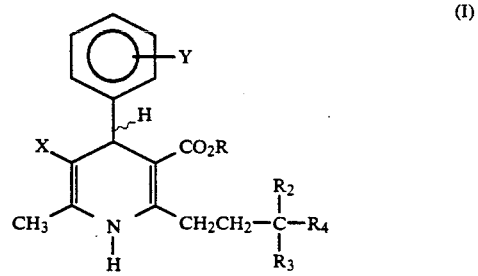

wherein X is —$CO_2R_1$, cyano, nitro, —$COCH_3$; each of R and $R_1$, which are the same or different, is a primary, secondary or tertiary, saturated or unsaturated, linear or branched $C_1$-$C_6$ alkyl group optionally substituted by one or more hydroxy, $C_1$-$C_7$-monoalkylamino, di-$C_1$-$C_7$-alkylamino, benzylamino, $C_1$-$C_6$-alkoxy, phenoxy groups which are optionally substituted; $R_2$ is hydrogen; $R_3$ is hydrogen or hydroxy, —$OCOR_5$, $OSO_2R_6$, azide, amino, —$NHPO(OR_7)_2$, —$NHCOR_5$, $C_1$-$C_4$-alkoxy or fluorine, chlorine, bromine or iodine, SH, $SCOR_6$ or $C_1$-$C_6$-alkylthio, phenylthio or benzylthio; $R_4$ is an optionally substituted aromatic or an optionally substituted 5- or 6-membered heteroaromatic group; Y is one or more substituents, which may be the same or different, selected from $C_1$-$C_4$-alkoxy, halogen, nitro, cyano, $C_1$-$C_6$-alkoxycarbonyl, $C_1$-$C_6$-alkylthio, halo-$C_1$-$C_6$-alkyl, halo-$C_1$-$C_6$-alkoxy, $NHCOR_5$ or $NHSO_2R_6$; $R_5$ is hydrogen or $C_1$-$C_4$-alkyl, trihalomethyl, $C_1$-$C_4$-alkoxy or phenyl, optionally substituted by one or more nitro, halogen, $C_1$-$C_4$ alkyl, $C_1$-$C_4$-alkoxy, amino; $R_6$ is hydrogen or a $C_1$-$C_4$-alkyl, trihalomethyl, phenyl or p-methylphenyl group; $R_7$ is $C_1$-$C_4$-alkyl or phenyl, are useful as antihypertensive, cytoprotecting or anti-ulcer agents.

5 Claims, No Drawings

ARALKYL-1,4-DIHYDROPYRIDINES, A METHOD FOR THEIR PREPARATION AND PHARMACEUTICAL COMPOSITION CONTAINING THEM

Object of the present invention are 2-alkyl-substituted-1,4-dihydropyridines, a method for their preparation and pharmaceutical compositions containing them.

The compounds of the invention have the following general formula I

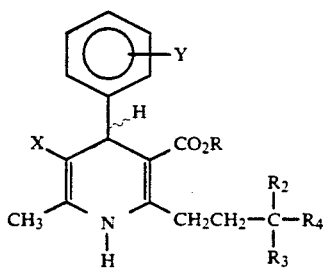

wherein:

X is a $-CO_2R_1$, cyano, nitro, $-COCH_3$ group;

R and $R_1$, that can be the same or different, are a primary, secondary or tertiary, saturated or unsaturated, linear or branched $C_1-C_6$ alkyl group that can be substituted or not by one or more hydroxy, $C_1-C_7$-monoalkylamino, di-$C_1-C_7$-alkylamino, benzylamino, $C_1-C_6$-alkoxy, phenoxy groups optionally substituted by one or more $C_1-C_6$ alkyl, $C_1-C_6$ alkoxy, halo-$C_1-C_6$ alkyl, halo-$C_1-C_6$-alkoxy, halogen, nitro, cyano, $C_1-C_6$ alkoxycarbonyl, $C_1-C_6$ alkylthio, NHCOR$_5$, SO$_2$R$_6$, $C_1-C_4$-alkylamino, di($C_1-C_4$)alkylamino, hydroxy;

$R_2$ is hydrogen;

$R_3$ is hydrogen or a hydroxy, $-OCOR_5$, $OSO_2R_6$, azide, amino, $-NHPO(OR_7)_2$, $-NHCOR_5$ group, a $C_1-C_4$-alkoxy group or a fluorine, chlorine, bromine or iodine atom, a SH group, a SCOR$_6$ or a $C_1-C_6$-alkylthio, phenylthio or benzylthio group;

$R_4$ is an optionally substituted aromatic or an optionally substituted 5- or 6-membered heteroaromatic group, containing one or more heteroatoms selected in the group of N,S,O, wherein the substituent is selected from one or more hydroxy, $C_1-C_7$-monoalkylamino, di-$C_1-C_7$-alkylamino, benzylamino, $C_1-C_6$-alkoxy, phenoxy groups optionally substituted by one or more $C_1-C_6$ alkyl, $C_1-C_6$ alkoxy, halo-$C_1-C_6$ alkyl, halo-$C_1-C_6$-alkoxy, halogen, nitro, cyano, $C_1-C_6$alkoxycarbonyl, $C_1-C_6$ alkylthio, NHCOR$_5$, SO$_2$R$_6$, $C_1-C_4$-alkylamino, di($C_1-C_4$)alkylamino, hydroxy;

Y is one or more substituents, that can be the same or different, selected in the group of $C_1-C_4$-alkoxy, halogen, nitro, cyano, $C_1-C_6$-alkoxycarbonyl, $C_1-C_6$-alkylthio, halo-$C_1-C_6$-alkyl, halo-$C_1-C_6$-alkoxy, NHCOR$_5$ or NHSO$_2$R$_6$;

$R_5$ is hydrogen or a $C_1-C_4$-alkyl, trihalomethyl, $C_1-C_4$-alkoxy or phenyl group, optionally substituted by one or more nitro, halogen, $C_1-C_4$-alkyl, $C_1-C_4$-alkoxy, amino groups;

$R_6$ is hydrogen or a $C_1-C_4$-alkyl, trihalomethyl, phenyl or p-methylphenyl group;

$R_7$ is a $C_1-C_4$-alkyl group or a phenyl group.

Included in the scope of the present invention are pharmaceutically acceptable salts, optical antipodes, i.e. the single enantiomers, their mixtures, the single enantiomers, their mixtures, the single diastereoisomers of formula I and their mixtures.

Pharmaceutically acceptable salts of compounds of formula I are those with pharmaceutically acceptable acids and bases.

Derivatives of 1,4-dihydropyridin-3,5-dicarboxylic acids, having in position 2 a (2-phenyl-2-hydroxy)-ethyl chain are claimed in Japanese Patent Application No. 8564692 Derivatives of 1,4-dihydropyridin-3,5-dicarboxylic acids, substituted in 2 position with a 3-oxo-1-propenyl chain are claimed in German Patent Application No. 2935772. In both cases there are evident structural differences between the cited compounds and the compounds of the present invention.

Alkyl, alkoxy, alkylthio, acyloxy and acylamino groups according to the invention may have both linear or branched chain; an unsaturated alkyl group of R or $R_1$ may be both a cis- or trans-$C_2-C_6$-alkenyl residue or a $C_2-C_6$-alkynyl residue, preferably propargyl.

According to the present invention, a halo-$C_1-C_6$-alkyl group is preferably trichloromethyl or trifluoromethyl; a halo-$C_1-C_6$-alkoxy group is preferably difluoromethoxy; a $C_1-C_6$-alkyl group is preferably methyl, ethyl, isopropyl or tertbutyl; a monoalkylamino group is preferably methyl-, ethyl-, isopropyl- or benzylamino; a dialkylamino group is preferably dimethyl-, diethyl-, N-methyl-N-benzylamino.

An aryl group of R or $R_1$ is preferably phenyl which can be substituted by one or more methyl, ethyl, methoxy, ethoxy, propoxy, trifluoromethyl, halogen, nitro, cyano, methylthio, acetamido, methansulfonamido.

An aromatic group of $R_4$ is preferably phenyl or phenyl substituted by methyl, ethyl, methoxy, ethoxy, propoxy, trifluoromethyl, halogen nitro, cyano, methylthio, acetamido, methanesulfonamide, methylamino, dimethylamino, diethylamino, N-piperidinyl, 4-morpholinyl, N-piperazinyl, hydroxy.

Preferred 5- or 6-membered heteroaromatic groups are thienyl, furanyl, pyridyl, pyrrolyl, pyrimidyl, pyridazyl, imidazolyl, oxazolyl, isooxazolyl, thiazolyl, triazolyl, pyrazinyl, thiazinyl group, also preferred 5- or 6-membered group are benzo condensed heteroaryl such as quinolyl, isoquinolyl, benzothienyl, quinazolyl, indolyl, benzofuranyl, indazolyl, benzooxazolyl, benzothiazolyl group.

Preferred $C_1-C_6$ alkylthio group are methylthio, ethylthio, butylthio, also preferred are benzylthio and phenylthio, while preferred acylthio group are formylthio acetylthio and benzoylthio, p-methylbenzoylthio.

The residue Y represents preferably one or more groups halogen nitro, cyano, methoxy, ethoxy, propoxy, methylthio, trifluoromethyl, acetamido, methansolfonamido.

$R_5$ represents preferably hydrogen, methyl, tertbutyl, ethoxy, trifluoroacetyl, acetyl, phenyl or phenyl substituted by one or more nitro, methoxy, halogen.

An alkyl group of $R_6$ represents preferably methyl. The trihalomethyl group is preferably trifluoromethyl.

The $-NHPO(OR_7)_2$ group represents preferably a $-NHPO(OC_2H_5)_2$ group.

Preferred compounds of the present invention are compounds of formula I, wherein:

X is carbomethoxy, carboethoxy, carboisopropoxy, cyano, COCH$_3$ or nitro;

R is ethyl;

$R_3$ is hydrogen, OH, OCOR$_5$, OS$_2$NHPO(OR$_7)_2$, azido, amido, $-NHCOR_5$, ethoxy, fluorine, bromine or chlorine;

R$_4$ is phenyl; phenyl substituted by methoxy, nitro or bromo; thienyl or pyridyl;

Y is nitro, chloro, fluoro, trifluoromethyl or methylthio, acetamido;

R$_5$ is hydrogen, methyl, trifluoromethyl, ethoxy, tert-butyl, phenyl or 4-nitrophenyl;

R$_6$ is methyl and

R$_7$ is ethyl.

The most preferred group of compounds are compounds wherein

X is carbomethoxy, carboethoxy, carboisopropoxy, cyano or nitro;

R is ethyl;

R$_3$ is hydrogen, OH, —OCOR$_5$, OSO$_2$R$_6$, azido, amino, —NHCOR$_5$, ethoxy, fluorine, bromine or chlorine;

R$_4$ is phenyl;

Y is nitro, chloro, trifluoromethyl or methylthio;

R$_5$ is hydrogen, trifluoromethyl or ethoxy;

R$_6$ is methyl.

Examples of preferred compounds of the invention are the following:

2-(3-formyloxy-3-phenylpropyl)-3-carboethoxy-5-carbomethoxy-4-(m-nitrophenyl)-6-methyl-1,4-dihydropyridine;

2-(3-formyloxy-3-phenylpropyl)-3-carboethoxy-5-carbomethoxy-4-(m-chlorophenyl)-6-methyl-1,4-dihydropyridine;

2-(3-formyloxy-3-phenylpropyl)-3-carboethoxy-5-carbomethoxy-4-(m-trifluoromethylphenyl)-6-methyl-1,4-dihydropyridine;

2-(3-trifluoroacetoxy-3-phenylpropyl)-3-carboethoxy-5-carbomethoxy-4-(m-nitrophenyl)-6-methyl-1,4-dihydropyridine;

2-(3-azido-3-phenylpropyl)-3-carboethoxy-5-carbomethoxy -4-(m-nitrophenyl)-6-methyl-1,4-dihydropyridine;

2-(3-phenyl-3-hydroxypropyl)-3-carboethoxy-5-carbomethoxy-4-(m-nitrophenyl)-6-methyl-1,4-dihydropyridine;

2-(3-phenyl-3-hydroxypropyl)-3,5-dicarboethoxy-4-(m-methylthiophenyl)-6-methyl-1,4-dihydropyridine;

2-(3-phenyl-3-hydroxypropyl)-3-carboethoxy-5-carbomethoxy-4-(m-trifluoromethylphenyl)-6-methyl-1,4-dihydropyridine;

2-(3-phenyl-3-hydroxypropyl)-3,5-dicarboethoxy-4-(m-chlorophenyl)-6-methyl-1,4-dihydropyridine;

2-(3-phenyl-3-bromopropyl)-3-carboethoxy-5-cyano-4-(m-nitrophenyl)-6-methyl-1,4-dihydropyridine;

2-(3-fluoro-3-bromopropyl)-3-carboethoxy-5-nitro-4-(m-nitrophenyl)-6-methyl-1,4-dihydropyridine;

2-(3-fluoro-3-phenylpropyl)-3-carboethoxy-5-cyano-4-(m-nitrophenyl)-6-methyl-1,4-dihydropyridine;

2-(3-azido-3-phenylpropyl)-3-carboethoxy-5-nitro-4-(m-nitrophenyl)-6-methyl-1,4-dihydropyridine;

2-(3-azido-3-phenylpropyl)-3-carboethoxy-5-carboisopropoxy-4-(m-nitrophenyl)-6-methyl-1,4-dihydropyridine;

2-(3-azido-3-phenylpropyl)-3-carboethoxy-5-carboethoxy-4-(m-chlorophenyl)-6-methyl-1,4-dihydropyridine;

2-(3-azido-3-phenylpropyl)-3-carboethoxy-5-carboethoxy-4-(m-methylthiophenyl)-6-methyl-1,4-dihydropyridine;

2-(3-phenyl-3-aminopropyl)-3-carboethoxy-5-carbomethoxy -4-(m-nitrophenyl)-6-methyl-1,4-dihydropyridine;

2-(3-phenyl-3-aminopropyl)-3-carboethoxy-5-carbomethoxy -4-(m-chlorophenyl)-6-methyl-1,4-dihydropyridine;

2-(3-phenyl-3-aminopropyl)-3-carboethoxy-5-carbomethoxy -4-(m-methylthiophenyl)-6-methyl-1,4-dihydropyridine;

2-(3-phenyl-3-aminopropyl)-3-carboethoxy-5-carbomethoxy -4-(m-trifluoromethylphenyl)-6-methyl-1,4-dihydropyridine;

2-[3-phenyl-3-(N-ethoxycarbonyl)aminopropyl]-3-carboethoxy-5-carbomethoxy-4-(m-nitrophenyl)-6-methyl-1,4-dihydropyridine;

2-(3-phenyl-3-formylaminopropyl)-3-carboethoxy-5-carbomethoxy-4-(m-nitrophenyl)-6-methyl-1,4-dihydropyridine;

2-(3-phenyl-3-formylaminopropyl)-3-carboethoxy-5-carbomethoxy-4-(m-chlorophenyl)-6-methyl-1,4-dihydropyridine 2-(3-phenyl-3-formylaminopropyl)-3-carboethoxy-5-carbomethoxy-4-(m-methylthiophenyl)-6-methyl-1,4-dihydropyridine;

2-(3-ethoxy-3-phenylpropyl)-3-carboethoxy-5-carbomethoxy-4-(m-nitrophenyl)-6-methyl-1,4-dihydropyridine;

2-(3-phenylpropyl)-3-carboethoxy-5-carbomethoxy-4-(m-nitrophenyl)-6-methyl-1,4-dihydropyridine;

2-(3-phenylpropyl)-3-carboethoxy-5-carbomethoxy-4-(m-chlorophenyl)-6-methyl-1,4-dihydropyridine;

2-(3-phenylpropyl)-3-carboethoxy-5-carbomethoxy-4-(m-methylthiophenyl)-6-methyl-1,4-dihydropyridine;

2-(3-methylsulfonyloxy-3-phenyl)propyl-3-carboethoxy-5-carbomethoxy-4-(m-nitrophenyl)-6-methyl-1,4-dihydropyridine;

2-(3-azido-3-phenylpropyl)-3-carboethoxy-5-cyano-4-(m-nitrophenyl)-6-methyl-1,4-dihydropyridine;

2-(3-chloro-3-phenylpropyl)-3,5-dicarboethoxy-4-(m-nitrophenyl)-6-methyl-1,4-dihydropyridine;

2-(3-chloro-3-phenylpropyl)-3-carboethoxy-5-carbomethoxy-4-(m-chlorophenyl)-6-methyl-1,4-dihydropyridine;

2-(3-chloro-3-phenylpropyl)-3-carboethoxy-5-carbomethoxy-4-(m-trifluoromethylphenyl)-6-methyl-1,4-dihydropyridine;

2-(3-chloro-3-phenylpropyl)-3-carboethoxy-5-carbomethoxy-4-(m-nitrophenyl)-6-methyl-1,4-dihydropyridine;

2-(3-chloro-3-phenylpropyl)-3-carboethoxy-5-carboisopropoxy-6-methyl-4-(m-nitrophenyl)-1,4-dihydropyridine;

2-(3-bromo-3-phenylpropyl)-3-carboethoxy-5-carbomethoxy -4-(m-nitrophenyl)-6-methyl-1,4-dihydropyridine;

2-(3-bromo-3-phenylpropyl)-3-carboethoxy-5-carbomethoxy -4-(m-chlorophenyl)-6-methyl-1,4-dihydropyridine;

2-(3-fluoro-3-phenylpropyl)-3-carboethoxy-5-carbomethoxy-4-(m-nitrophenyl)-6-methyl-1,4-dihydropyridine;

2-(3-fluoro-3-phenylpropyl)-3-carboethoxy-5-carbomethoxy-4-(m-methylthiophenyl)-6-methyl-1,4-dihydropyridine;

2-[3-formyloxy-3-(pyrid-3-yl)propyl]-3,5-dicarboethoxy-4-(m-methylthiophenyl)-6-methyl-1,4-dihydropyridine;

2-[3-formyloxy-3-(4-methoxyphenyl)propyl]-3,5-dicarboethoxy-4-(m-methylthiophenyl)-6-methyl-1,4-dihydropyridine;

2-[3-hydroxy-3-(4-nitrophenyl)propyl]-3,5-dicarboethoxy -4-(m-methylthiophenyl)-6-methyl-1,4-dihydropyridine;

2-[3-hydroxy-3-(3-thienyl)propyl]-3-carboethoxy-5-carbomethoxy-4-(m-nitrophenyl)-6-methyl-1,4-dihydropyridine;

2-[3-chloro-3-(3-thienyl)propyl]-3,5-dicarboethoxy-4-(m -nitrophenyl)-6-methyl-1,4-dihydropyridine;

2-[3-chloro-3-(4-methoxyphenyl)propyl]-3,5-dicarboethoxy-4-(m-methylthiophenyl)-6-methyl-1,4-dihydropyridine;

2-[3-(4-methoxyphenyl)-3-aminopropyl]-3,5-dicarboethoxy -6-methyl-4-(m-methylthiophenyl)-1,4-dihydropyridine;

2-[3-(pyrid-3-yl)-3-aminopropyl]-3,5-dicarboethoxy-6-methyl-4-(m-methylthiophenyl)-1,4-dihydropyridine;

2-[3-acetamido-3-(2-thienyl)propyl]-3-carboethoxy-5-carbomethoxy-4-(m-nitrophenyl)-6-methyl-1,4-dihydropyridine;

2-[3-acetamido-3-(4-methoxyphenyl)propyl]-3,5-dicarboethoxy-4-(m-methylthiophenyl)-6-methyl-1,4-dihydropyridine; nitrophenyl)-6-methyl-1,4-dihydropyridine;

2-(3-phenyl-3-methylthiopropyl)-3-carbomethoxy-5-carboethoxy-4-(m-chlorophenyl)-6-methyl-1,4-dihydropyridine;

2-(3-phenyl-3-acetylthiopropyl)-3,5-dicarbomethoxy-(m-trifluoromethylphenyl)-6-methyl-1,4-dihydropyridine.

The compounds of the invention are prepared by a process including cleavage of the cyclopropane ring of a compound of formula II:

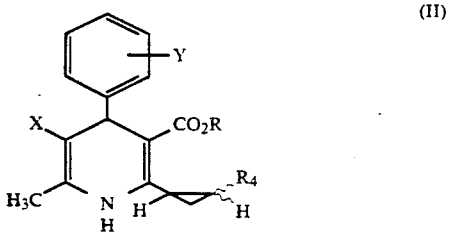

wherein R, R$_4$, X and Y are as above defined, with a mineral or a monobasic organic acid such as hydrazoic acid (HN$_3$), hydrogen fluoride (HF), hydrogen chloride (HCl), hydrogen bromide (HBr), hydrogen iodide (HJ), hydrogen sulphide (H$_2$S), monobasic carboxylic acids (e.g. formic, acetic, propionic, trifluoroacetic, benzoic acid) or sulpyhonic acids (e.g. methanesulphonic, trifluoromethansulphonic, to give a compound of formula Ia

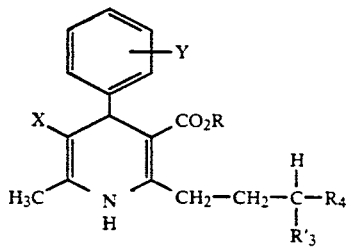

wherein X, Y, R and R$_4$ are as above defined, while R'$_3$ is an azide group, an halogen, a —OCOR$_5$, a —OSO$_2$R$_6$ group, a mercapto group, R$_5$ and R$_6$ being as above defined, that is then transformed into another compound I by hydrolysis of an ester group to give an alcohol, that, on its turn, is etherified or esterified; by substitution of a halogen or of a —OSO$_2$R$_6$ group with an azide group, an alkylmercaptan or an acylthio group; a reduction of an azide group to a primary amino group that, if desired, is then alkylated or acylated; by reductive substitution of a sulphonate or halogen derivative to alkane by acylation or alkylation of a mercapto group, and, if desired, a compound of formula I can be further submitted to optical or diastereoisomer resolution and salification.

The cleavage reaction of the cyclopropane ring of a compound II, to give a compound Ia is carried out with a molar excess of monobasic mineral or organic acid, preferably in presence of a co-solvent such as alcohols (e.g. methanol, ethanol, isopropanol), ethers (e.g. tetrahydrofuran, dioxane, 1,2-dimethoxyethane), halogenated solvents (e.g. dichloromethane, chloroform, 1,2-dichloroethane), water and mixtures thereof.

The reaction temperature ranges from —30° C. to the solvent's reflux temperature, for reaction times varying from few minutes to 48 hours, but preferably the reaction is carried out at a temperature ranging from 0° C. to the room temperature for a time ranging from 10 minutes to some hours.

The compounds Ia, if desired, can be further transformed into other compounds I, by reaction known in the art, such as, for instance:

selective hydrolysis of ester group R'$_3$ in aqueous alcohols in presence of alkaline carbonate, bicarbonate, hydroxides (such as, for instance, lithium hydroxide, sodium hydroxide, sodium or potassium bicarbonate) at room temperature in a few hours. The obtained alcohols of general formula I (R$_3$=OH) can then be etherified or esterified by conventional methods;

reduction of an azide group to an amino group, e.g. by reaction with a trialkylphosphite in benzene or toluene and subsequent hydrolysis with aqueous mineral acids of the intermediate nitrogen-ylide or alternatively by reduction with sodium or lithium borohydrides in the presence of an alcohol such as methanol or ethanol, whereafter, if desired, the obtained primary amine of general formula I is alkylated or acylated by conventional methods;

reductive substitution of a halogen or sulphonated R'$_3$ group to alkane by reaction with tributyltinhydride in an inert solvent, such as benzene or toluene, optionally in presence of a radical promoter, such as azobisisobutyronitrile, or alternatively by reaction with LiAlH$_4$ in ethers.

The compounds of formula II are described in EP-A-215520.

The preferred compounds of formula II are the single cis- or trans-cyclopropyldiastereoisomers.

Cis- or trans-geometrical configuration of cyclopropane ring of compounds II is pre-determined by cis- or trans-configuration of β-ketoester of general formula III

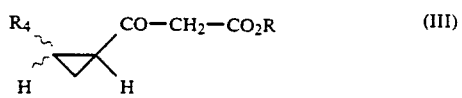

wherein R$_4$ and R are as above defined, used in the preparation of said compounds II, in accordance with the preferred preparation method of the above cited patent application.

The compounds II used in the present invention may be both cis- or trans-cyclopropyldiastereoisomers.

It has now been found that the cleavage of the cyclopropane ring (both cis- or trans) of compounds II by means of a monobasic mineral or organic acid occurs in a regio- and stereo-specific way, so starting from a single diastereoisomer of formula II, a single diastereoisomer of formula Ia is obtained and the subsequent optional transformation occurs in a stereospecific way.

Moreover, by using optically pure diastereoisomers of formula II, pure enantiomers of formula Ia are obtained.

Compounds of formula I are thus prepared, starting from single cis- or single trans-cyclopropyl-diastereoisomers of formula II, obtaining the single diastereoisomers of general formula Ia.

Use of diastereoisomeric mixtures of cis- or trans-cyclopropanes of formula II gives the same diastereoisomeric mixture of compounds of general formula Ia, that, if desired, can be separated into the single diastereoisomers.

Cis- and trans-cyclopropane of formula III are prepared according to known methods, starting from the corresponding cis- or trans-cyclopropane acids of formula IV:

wherein $R_4$ is as above defined.

The most useful methods for preparing compounds III starting from compounds IV are well known in the art and comprise the reaction of the acyl chloride of compounds IV either with monoethyl malonate, in the presence of magnesium ethylate, or with Meldrum's acid, in the presence of pyridine.

Compounds of formula IV are known both as racemates and single optical antipodes. For instance, in a recent publication (J. Arai et al., J. Am. Chem. Soc. 107, 8254–8256, 1985) an improvement in the synthesis of chiral cyclopropane acids, starting from ketals of $\alpha$-$\beta$-unsatured aldehydes, is disclosed.

Using optically pure $\gamma$-$\delta$-cyclopropan-$\beta$-ketoester of formula II in the Hantzsch cyclisation to dihydropyridine II, a mixture of optically active diastereoisomer II is obtained, that can be separated in the single chiral diastereoisomer by fractional crystallization or by chromatography.

Using the racemic mixture of $\gamma$-$\delta$-cyclopropan-$\beta$-ketoester of formula III, the mixture of racemic diastereoisomer of formula II is obtained, that can be separated in the single racemic diastereoisomer by fractional crystallization or by chromatography.

When administered by the oral route to conscious spontaneously hypertensive rats (SHR), or to hypertensive rat with hypertension induced by administration of deoxicorticosterone acetate (DOCA rats), the compounds of the invention cause a significant, long-lasting, dose-dependent decrease of the mean blood pressure.

The decrease of blood pressure takes place gradually, reaching its maximum effect after 6-8 hours from the administration, and the effect lasts for further 8-10 hours. For some compounds of the invention said antihypertensive effect is already evident also at low dosages such as 0.2-0.4 mg/kg by os; for example, 4-(R,S)-3'-(R,S)-2-(3'-chlorophenyl)-4-(m-nitrophenyl)-6-methyl-5-carbomethoxy-3-carboethoxy-1,4-dihydropyridine causes a decrease of 40 mmHg (18%) of mean blood pressure when administered at 0.2 mg/kg per os to SHR rats, and this effects lasts more than 12 hours.

Surprisingly, the compounds of formula I are from moderately to sparely active when tested in the classical Godfraind test (Arch. Int. Pharmacol. 172, 235, 1968) compared to nifedipine (from 10 to 1000 times less active).

When tested in vitro, the compounds of the invention are active in the inhibition of spontaneous lipidic peroxidation in homogenized rat brain.

The compounds of the invention are then useful as antihypertensive agents for treatment of circulatory diseases of different seriousness and etiology, and for treatment of thromboembolic diseases, in heart, kidney and brain ischaemia.

Compounds of the invention can be further used as cytoprotecting and anti-ulcer agents.

The compounds of the invention are characterized by high $LD_{50}$ values ranging from 400 mg/kg to more than 1000 mg/kg (in mice, both by oral and intraperitoneal route).

According to the above described pharmaco-toxicological results, the compounds of the invention are considered particulary useful in treatment of different hypertensive conditions, obtaining a progressive reduction of hypertension by administration of compounds of formula I at low doses (preferably one administration every 12-24 hours).

The compounds may be administered in various manners to achieve the desired effect. The compounds may be administered alone or in the form of pharmaceutical preparations to the patient being treated either orally or parenterally, such as, intraveneously or intramuscolarly. The formulation of suitable pharmaceutical compositions can be carried out by the skilled man according to the general common knowledge in the art, and referring to reference books, such as the "Remington's Pharmaceutical Sciences" Handbook, Mack Publishing Company, U.S.A.

The amount of compound administered will vary with the severity of the hypertension, and the mode of administration. For oral administration the antihypertensively effective amount of compound is from about 0.01 mg/kg (milligrams per kilograms body weight) per day to about 10 mg/kg per day and preferably from about 0.05 mg/kg per day to 5 mg/kg per day.

For parenteral administration the antihypertensively effective amount of compound is from about 0.001 mg/kg per day up to about 5 mg/kg per day and preferably from about 0.01 mg/kg per day up to about 2 mg/kg per day.

For oral administration a unit dosage may contain, for example, from 0.50 to 70 mg of the active ingredient. Since the compounds of the invention generally possesses a long lasting duration of action, they might be conveniently administered once or twice a day, however, repetitive daily administrations may be, at least in some instances, desirable and will vary with the conditions of the patient and the mode of administration. As used herein, the term "patient" is taken to mean a warm blooded animal, humans included.

For oral administration the compounds can be formulated into solid or liquid preparations such as capsules, pills, tablets, troches, powders, solutions, suspensions or emulsions. The solid unit dosage forms can be a capsule which can be of the ordinary gelatin type, either hard or soft, containing for example lubricants and inert fillers, such as lactose, sucrose and cornstarch.

In another embodiment, the compounds of the invention can be tabletted with conventional tablet bases such as lactose, sucrose and cornstarch in combination with binders such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compound in a physiologicaly acceptable diluent with a pharmaceutical carrier which can be a sterile liquid such as water and oils with or without the addition of a surfactant and other pharmaceutically acceptable adjuvants. Examples of oils which can be used in these preparations are those of mineral petroleum, animal, vegetable or synthetic origin. For example, peanut oil, soybean oil and mineral oil. In general, water, saline, aqueous dextrose and related sugar solutions, ethanol and glycols such as propylene glycol or polyethylene glycol can be used as liquid carriers for injectable solutions.

For rectal administration the compounds are administered in the form of suppositories, admixed with conventional vehicles such as, for example, cocoa butter, wax, spermaceti, polyvinylpyrrolidone, or polyoxyethylenglycols and their derivatives.

The preferred administration route for compounds of the invention is the oral route.

The following examples illustrate but do not limit the invention.

PREPARATION 1

A solution of ethyl trans-3-(2-phenyl-1-cyclopropyl)-2-(m-nitrophenylmethylen}-3-oxo-propanoate (5 g) and methyl 3-amino-crotonate (1.5 g) in ethanol is refluxed for 4 hours, then it is evaporated under vacuum and the residue is dissolved in ethyl acetate (60 ml), washed with water (3×10 ml), dried on sodium sulphate and purified on silica gel (300 g; eluent isopropyl ether) to give 4 g of a mixture of diastereoisomers trans-2-(2-phenyl-1-cyclopropyl)-3-carboethoxy-5-carbomethoxy-4-(m-nitrophenyl)-6-methyl-1,4-dihydropyridine, m.p. 123–125° C.

The diastereoisomeric mixture, showing in TLC (Merck-Kieselgel 60 F-254; eluent isopropyl ether) two spots at Rf 0.37 and Rf 0.42 of equal intensity, is purified with silica gel by chromatography (240 g; eluent: dichloroethane/isopropyl ether/hexane: 15/15/70), to give the two pure diastereoisomers trans-2-(2-phenyl-1-cyclopropyl)-carboethoxy-5-carbomethoxy-4-(m -nitrophenyl)-6-methyl-1,4-dihydropyridine; the less polar diastereoisomer (TLC - Merck Kieselgel 60; eluent isopropyl ether Rf 0.42), recrystallized from methanol (g 1/ ml 12), has a m.p. 135–137° C.; the more polar diastereoisomer (TLC—Merck Kieselgel 60; eluent isopropyl ether; Rf=0.37), recrystallized from methanol (g 1/ml 20), has m.p. 144–145° C.

PREPARATION 2

In accordance with procedure and conditions described for preparation 1, the following compounds were obtained (as diastereoisomeric mixture):
trans-2-(2-phenyl-1-cyclopropyl)-3-carboethoxy-5-cyano-4-(m-nitrophenyl)-6-methyl-1,4-dihydropyridine;
trans-2-(2-phenyl-1-cyclopropyl)-3-carboethoxy-5-nitro-4-(m-nitrophenyl)-6-methyl-1,4-dihydropyridine;
trans-2-(2-phenyl-1-cyclopropyl)-3-carboethoxy-5-methylcarbonyl-4-(m-nitrophenyl)-6-methyl-1,4-dihydropyridine;
cis-2-(2-phenyl-1-cyclopropyl)-3,5-dicarboethoxy-4-(m-nitrophenyl)-6-methyl-1,4-dihydropyridine;
cis-2-(2-phenyl-1-cyclopropyl)-3,5-dicarbomethoxy-4-(m-chlorophenyl)-6-methyl-1,4-dihydropyridine;
trans-2-[2-(pyrid-3-yl)-1-cyclopropyl]-3,5-dicarboethoxy-4-(m-methylthiophenyl)-6-methyl-1,4-dihydropyridine;
trans-2-[2-(4-methoxyphenyl)-1-cyclopropyl]-3,5-dicarboethoxy-4-(m-methylthiophenyl)-6-methyl-1,4-dihydropyridine;
trans-2-[2-(4-nitrophenyl)-1-cyclopropyl]-3,5-dicarboethoxy-4-(m-methylthiophenyl)-6-methyl-1,4-dihydropyridine.

EXAMPLE 1

A solution of the less polar diastereoisomer of trans-2-(2-phenyl-1-cyclopropyl)-3-carboethoxy-5-carbomethoxy-4-(m-nitrophenyl)-6-methyl-1,4-dihydropyridine (2.5 g) in formic acid (97%, 50 ml) is stirred for 30' at 25° C. under nitrogen atmosphere, then it is poured into water (200 ml) and extracted with ethyl ether (100 ml).

The organic phase is washed with a 5% $NaHCO_3$ aqueous solution (3×50 ml) and water (2×50 ml). The organic phase is dried ($Na_2SO_4$), filtered and evaporated. 2.68 g of the most polar diastereoisomer of 2-(3-phenyl-3-formyloxypropyl)-3-carboethoxy-5-carbomethoxy-4-(m-nitrophenyl)-6-methyl-1,4-dihydropyridine are obtained as a yellow glassy foam.

NMR ($\delta CDCl_3$) 8.2 (s,1H); 7.2–7.9 (m, 9H); 6.5 (sb, 1H);
5.4 (t,1H); 5.1 (s,1H); 4.1 (q,2H); 3.6 (s,3H); 1.9–2.9 (m,4H); 2.3 (s,3H ; 1.2 (t,3H).

Using in the above conditions the most polar diastereoisomer of trans-2-(2-phenyl-1-cyclopropyl)-3-carboethoxy-5-carbomethoxy-6-methyl-4-(m-nitrophenyl)-1,4-dihydropyridine, the less polar diastereoisomer of 2-(3-phenyl-3-formyloxypropyl)-3-carboethoxy-5-carbomethoxy-6-methyl-4-(m-nitrophenyl)-1,4-dihydropyridine is obtained.

NMR ($\delta CDCl_3$) 8.2 (s,1H); 7.2–7.9 m, 9H); 6.6 (sb, 1H);
5.5 (t,1H); 5.2 (s,1H); 4.2 (q,2H); 3.6 (s,3H); 1.9–2.8 (m,4H); 2.2 (s,3H); 1.1 (t,3H).

Operating in the same conditions, but using the mixture of diastereoisomers trans-2-(2-phenyl-1-cyclopropyl)-3-carboethoxy-5-carbomethoxy-4-(m-chlorophenyl)-6 -methyl-1,4-dihydropyridine, trans-2-(2-phenyl-1-cyclopropyl)-3-carboethoxy-5-carbomethoxy-4-(m-trifluoromethylphenyl) -6-methyl-1,4-dihydropyridine, and trans-2-(2-phenyl-1-cyclopropyl)-3-carboethoxy-5-carbomethoxy-4-(m-nitrophenyl)-6-methyl-1,4-dihydropyridine, the following diastereoisomeric mixtures are obtained:
2-(3-phenyl-3-formyloxypropyl)-3-carboethoxy-5-carbomethoxy-4-(m-chlorophenyl)-6-methyl-1,4-dihydropyridine;
2-(3-phenyl-3-formyloxypropyl)-3-carboethoxy-5-carbomethoxy-4-(m-trifluoromethylphenyl)-6-methyl-1,4-dihydropyridine;

2-(3-phenyl-3-formyloxypropyl)-3-carboethoxy-5-carbomethoxy-4-(m-nitrophenyl)-6-methyl-1,4-dihydropyridine.

EXAMPLE 2

A solution of trans-2-thienyl-1-cyclopropylcarboxylic acid (10 g, prepared according to J. W. McFarlan, J. Org. Chem. 30, 3298 (1965)) in thionyl chloride (10 ml) is stirred at room temperature for 24 hours; after usual work up the acyl chloride obtained (7.5 g) is dropped at 0° C. into a solution of Meldrum acid (5.8 g) and pyridine (8.0 g) in dichloromethane (80 ml).

After 4 hours at room temperature, water (ml 20) is added the two phase are separated and the organic one is washed ($NaHCO_3$ 3×10 ml, water 3×20 ml), dried ($Na_2SO_4$) and evaporated. The residue is dissolved in ethanol (100 ml) and the solution is heated at reflux for 2 hours; the reaction mixture is then evaporated and the obtained crude ethyl 2-(2-thienyl-1-cyclopropyl)-3-oxopropanoate (6 g) is used as such in the following reaction. It is reacted with m-nitrobenzaldehyde (3.8 g) in benzene (70 ml) in presence of piperidine acetate (2.0 g) as catalyst. The reaction mixture is refluxed for 8 hours, then it is cooled to room temperature, washed with water (3×15 ml), dried and evaporated.

The obtained mixture of cis- and trans-isomers of ethyl 3-[2-(2-thienyl)-1-cyclopropyl]-3-oxo-2-(m-nitrophenylmethylen)propanoate (7.0 g) is dissolved in ethanol (70 ml) in the presence of methyl-3-amino crotonate (2.2 g). The solution is refluxed for 6 hours, then evaporated in vacuum and the residue purified by chromatography (silica gel 200 g: diisopropyl ether) to give 4.8 g of trans-2-2-(2-thienyl)cyclopropyl]-3-carboethoxy-5-carbomethoxy-4-(m-nitrophenyl)-6-methyl-1,4-dihydropyridine (diastereoisomeric mixture).

A solution of said dihydropyridine (2.0 g) in formic acid (99%, 40 ml) is stirred for 45 minutes at 25° C. The reaction mixture is finally poured into water (300 ml) and extracted with diethyl ether (100 ml).

After usual work-up, 1.5 g of 2-[3-(2-thienyl)-3-formyloxypropyl]-3-carboethoxy-5-carbomethoxy-4-(m-nitrophenyl)-6-methyl-1,4-dihydropyridine, are obtained.

NMR ($\delta CDCl_3$) 8.1 (s,1H); 7.9-6.5 (m,8H); 5.3 (t,1H); 5.1 (s,1H); 4.1 (q,2H); 3.6 (s,3H);
2.9-1.9 (m,4H); 2.3 (s,3H); 1.2 (t,3H).

EXAMPLE 3

Using the experimental conditions of examples 1 and 2, the following 6-methyl-1,4-dihydropyridines were obtained, (as diastereoisomeric mixtures):

2-(3-formyloxy-3-phenylpropyl)-3-carboethoxy-5-cyano-4-(m-nitrophenyl);

2-(3-formyloxy-3-phenylpropyl)-3-carboethoxy-5-nitro-4-(m-nitrophenyl);

2-(3-formyloxy-3-phenylpropyl)-3-carboethoxy-5-methylcarbonyl-4-(m-nitrophenyl);

2-(3-formyloxy-3-phenylpropyl)-3,5-dicarboethoxy-4-(m-nitrophenyl);

2-(3-formyloxy-3-phenylpropyl)-3,5-dicarboethoxy-4-(m-chlorophenyl);

2-[3-(pyrid-3-yl)-3-formyloxypropyl]-3,5-dicarboethoxy-4-(m-methylthiophenyl);

2-[3-formyloxy-3-(4-methoxyphenyl)propyl]-3,5-dicarboethoxy-4-(m-methylthiophenyl);

2-[3-formyloxy-3-(4-nitrophenyl)propyl]-3,5-dicarboethoxy-4-(m-methylthiophenyl).

EXAMPLE 3a

Trifluoroacetic acid (1 ml) is dropped under inert atmosphere ($N_2$) at room temperature in a solution of trans-2-(2-phenyl-1-cyclopropyl)-3-carboethoxy-5-carbomethoxy-4-(m-nitrophenyl)-6-methyl-1,4-dihydropyridine (0.1 g; mixture of diastereoisomers). After 3 hours the mixture is worked up as described in example 1, and the crude residue is purified by chromatography (silica gel 5 eluent: isopropyl ether/hexane 60:40). 20 mg of diastereoisomeric mixture of 2-(3-phenyl-2-trifluoroacetoxypropyl)-3-carboethoxy-5-carbomethoxy-4-(m-nitrophenyl)-6-methyl-1,4-dihydropyridine are obtained as a glassy yellow foam.

NMR ($\delta CDCl_3$) 8.0-7.2 (m,9H); 6.5 (sb,1H); 5.7 (t,1H);
5.2 (s,1H); 4.2 (q,2H); 3.5 (S,3H); 1.9-2.7 (m,4H); 2.2 (s,3H); 1.1 (t,3H).

Using in the above conditions the diastereoisomeric mixture of trans-2-(2-phenyl-1-cyclopropyl)-3-carboethoxy-5-carbomethoxy-4-(m-chlorophenyl)-6-methyl-1,4-dihydropyridine and trans-2-(2-phenyl-1-cyclopropyl)-3-carboethoxy-5-carbomethoxy-4-(m-methylthiophenyl)-6-methyl-1,4-dihydropyridine, the following diastereoisomeric mixtures are obtained:

2-(3-phenyl-3-trifluoroacetoxypropyl)-3-carboethoxy-5-carbomethoxy-4-(m-chlorophenyl)-6-methyl-1,4-dihydropyridine;

2-(3-phenyl-3-trifluoroacetoxypropyl)-3-carboethoxy-5-carbomethoxy-4-(m-methylthiophenyl)-6-methyl-1,4-dihydropyridine.

EXAMPLE 4

0.45 ml of methansulphonic acid are added under inert atmosphere at 25° C. to a solution of trans-2-(2-phenyl-1-cyclopropyl)-3-carboethoxy-5-carbomethoxy-4-(m-nitrophenyl)-6-methyl-1,4-dihydropyridine (50 mg diastereoisomeric mixture) in chloroform (5 ml), after 1.5 hours the reaction mixture is poured into iced water and extracted with diethyl ether (20 ml).

The organic phase is washed with an $NaHCO_3$ 5% aqueous solution (3×20 ml) and with water (2×30 ml), then it is dried on sodium sulphate, filtered and The crude compound is purified by chromatography (silica 5 g; eluent isopropyl ether/hexane 60/40). 25 g of 2-(3-phenyl-3-methylsulphonyloxypropyl)-3-carboethoxy-5-carbomethoxy-6-methyl-4-(m-nitrophenyl)-1,4-dihydropyridine (diastereoisomeric mixture) are obtained as an amorphous yellow solid.

NMR ($\delta CDCl_3$) 8.0-7.2 (m,9H); 6.5 (sb,1H); 5.7 (t,1H);
5.2 (s,1H); 4.2 (q,2H); 3.5 (s,3H); 3.0 (s,3H); 1.9-2.7 (m,4H); 2.2 (s,3H);
1.0 (t,3H).

Using in the same conditions a diastereoisomeric mixtures of trans-2-(2-phenyl-1-cyclopropyl)-3-carboethoxy-5-carbomethoxy-4-(m-chlorophenyl)-6-methyl-1,4-dihydropyridine and of trans-2-(2-phenyl-1-cyclopropyl)-3-carboethoxy-5-carbomethoxy-6-methyl-4-(o-trifluoromethylphenyl)-1,4-dihydropyridine, the following diastereoisomeric mixtures are obtained:

2-(3-phenyl-3-methylsulphonyloxypropyl)-3-carboethoxy-5-carbomethoxy-6-methyl-4-(m-chlorophenyl)-1,4-dihydropyridine;

2-(3-phenyl-3-methylsulphonyloxypropyl)-3-carboethoxy-5-carbomethoxy-6-methyl-4-(o-trifluoromethylphenyl)-1,4-dihydropyridine.

EXAMPLE 5

A chloroform solution (5 ml) of trans-2-(2-phenyl-1-cyclopropyl)-3-carboethoxy-5-carbomethoxy-4-(m-nitrophenyl)-6-methyl-1,4-dihydropyridine (500 mg, diastereoisomeric mixture) and hydrazoic acid (5% solution in chloroform, 5 ml) is heated in a sealed tube under $N_2$ atmosphere at 80° C. for two hours.

The mixture is cooled at 0° C., then the tube is opened and the mixture is poured in $H_2O$/ice (25 ml) and diethyl ether (20 ml). The phases are separated and the organic one is washed with a 5% $NaHCO_3$ aqueous solution (25 ml) and water, dried on sodium sulphate and evaporated. A crude red glassy oil is obtained (0.5 g) that is purified by column chromatography (eluent isopropyl ether/silica 20 g), obtaining 25 mg of 2-(3-phenyl-3-azidopropyl)-3-carboethoxy-5-carbomethoxy-6 -methyl-4-(m-nitrophenyl)-1,4-dihydropyridine (yellow glassy oil) as a diastereoisomeric mixture.

NMR ($\delta CDCl_3$) 7.9–7.2 (m,9H); 6.6 (sb,1H); 5.3 (t, 1H);

5.2 (s,1H); 4.1 (q,2H); 3.6 (s,3H);

2.9–1.9 (m,4H); 2.3 (s,3H); 1.2 (t,3H).

Using in the above conditions only one diastereoisomer of trans-2-(2-phenyl-1-cyclopropyl)-3-carboethoxy-5-carbomethoxy-6-methyl-4-(m-nitrophenyl)-1,4-dihydropyridine, only one diastereoisomer of 2-(3-phenyl-3-azidopropyl)-3-carboethoxy-5-carbomethoxy-6 -methyl-4-(m-nitrophenyl 1,4-dihydropyridine is For instance, starting from the less polar diastereoisomer (m.p. 135–137° C.) the less polar azido derivative is obtained (m.p. 128–131° C).

EXAMPLE 6

0.3 ml of 5% $NaHCO_3$ aqueous solution are added to a solution of the most polar diastereoisomer of 2-[3-formyloxy-3-phenyl-propyl]-3-carboethoxy-5-carbomethoxy-4-(m-nitrophenyl)-6-methyl-1,4-dihydropyridine (2.5 g) in methanol (20 ml). The mixture is refluxed for 30 minutes, then it is cooled to 25° C. and evaporated to a small volume (2 ml) under reduced pressure. The sticky mass is diluted with ethyl ether (70 ml) and water (30 ml) and the phases are separed. The organic phase is washed with water (2×30 ml) and dried on sodium sulphate. The solvent is evaporated under reduced pressure, obtaining 2.3 g of the most polar diastereoisomer of 2-(3-phenyl-3-hydroxy-propyl)-3-carbomethoxy-5-carboethoxy-6-methyl-4-(m-nitrophenyl)-1,4-dihydropyridine as yellow foam.

NMR ($\delta CDCl_3$) 7.9–7.2 (m,9H); 6.5 (sb,1H); 5.2 (s,1H);

5.1 (t,1H); 4.1 (q,2H); 3.6 (s,3H); 2.9–1.9 (m,5H); 2.3 (s,3H); 1.2 (t,3H).

In the same way, the following compounds were obtained:

2-(3-phenyl-3-hydroxypropyl)-3-carboethoxy-5-carbomethoxy-4-(o-methylthiophenyl)-6-methyl-1,4-dihydropyridine;

2-(3-phenyl-3-hydroxypropyl)-3,5-dicarboethoxy-4-(m-methylthiophenyl)-6-methyl-1,4-dihydropyridine;

2-(3-phenyl-3-hydroxypropyl)-3,5-dicarboethoxy-4-(o-methylthiophenyl)-6-methyl-1,4-dihydropyridine;

2-(3-phenyl-3-hydroxypropyl)-3-carboethoxy-5-carboisopropoxy-4-(p-fluorophenyl)-6-methyl-1,4-dihydropyridine;

2-(3-phenyl-3-hydroxypropyl)-3-carboethoxy-5-cyano-4-(m -nitrophenyl)-6-methyl-1,4-dihydropyridine;

2-(3-phenyl-3-hydroxypropyl)-3-carboethoxy-5-nitro-4-(m -nitrophenyl)-6-methyl-1,4-dihydropyridine;

2-(3-phenyl-3-hydroxypropyl)-3,5-dicarboethoxy-4-(o-nitrophenyl)-6-methyl-1,4-dihydropyridine;

2-(3-phenyl-3-hydroxypropyl)-3,5-dicarboethoxy-4-(m-chlorophenyl)-6-methyl-1,4-dihydropyridine;

2-(3-phenyl-3-hydroxypropyl)-3,5-dicarboethoxy-4-(2-nitro-5-methylthiophenyl)-6-methyl-1,4-dihydropyridine;

2-[3-hydroxy-3-(pyrid-3-yl)propyl]-3,5-dicarboethoxy-4-(m-methylthiophenyl)-6-methyl-1,4-dihydropyridine;

2-[3-hydroxy-3-(4-methoxyphenyl)propyl]-3,5-dicarboethoxy-4-(m-methylthiophenyl)-6-methyl-1,4-dihydropyridine;

2-[3-hydroxy-3-(4-nitrophenyl)propyl]-3,5-dicarboethoxy-4-(m-methylthiophenyl)-6-methyl-1,4-dihydropyridine;

2-[3-hydroxy-3-(2-thienyl)propyl]-3-carboethoxy-5-carthoxy-4-(m-nitrophenyl)-6-methyl-1,4-dihydropyridine;

2-[3-hydroxy-3-(3-thienyl)propyl]-3-carboethoxy-5-carbomethoxy-4-(m-nitrophenyl)-6-methyl-1,4-dihydropyridine;

2-(3-phenyl-3-hydroxypropyl)-3-carboethoxy-5-carbomethoxy-6-methyl-4-(m-chlorophenyl)-1,4-dihydropyridine;

2-(3-phenyl-3-hydroxypropyl)-3-carboethoxy-5-carbomethoxy-6-methyl-4-(m-trifluoromethylphenyl)-1,4-dihydropyridine;

2-(3-phenyl-3-hydroxypropyl)-3-carboethoxy-5-carbomethoxy-6-methyl--4-(m.-methylthiophenyl)-1,4-dihydropyridine.

EXAMPLE 7

A solution of hydrogen chloride (gas) in absolute ethanol (8N solution, ml 10) is dropped at 0° C. in a suspension of the less polar diastereoisomer of trans-2-(2-phenyl-1-cyclopropyl)-3-carboethoxy-5-carbomethoxy-4-(m-nitrophenyl)-6-methyl-1,4-dihydropyridine (m.p. 135–137° C.; 4 g) in ethanol (20 ml).

After 20 minutes of stirring at room temperature the clear solution is evaporated in vacuum. The residue is dissolved in ethyl ether (200 ml), washed with water (3×20 ml), sodium bicarbonate 5% solution; 2×10 ml), water (2×20 ml) and dried on sodium sulphate.

The organic phase is evaporated in vacuum, the residue is triturated in ethyl ether (30 ml) and stirred at 0° C. for 12 hours.

The formed crystals are filtered and washed with ice-cooled ether.

2.97 g of the most polar diastereoisomer of 2-(3-phenyl-3-chloropropyl)-3-carboethoxy-5-carbomethoxy-(m-nitrophenyl)-6-methyl-1,4-dihydropyridine, m.p. 119–120° C., are obtained.

Using in the above conditions, the most polar diastereoisomer of trans-2-(2-phenyl-1-cyclopropyl)-3-carboethoxy-5-carbomethoxy-4-(m-nitrophenyl)-6-methyl-1,4-dihydropyridine, the less polar diastereoisomer of 2-(3-phenyl-3-chloropropyl)-3-carboethoxy-5-carbomethoxy-(m-nitrophenyl)-6-methyl-1,4-dihydropyridine, m.p 137–139° C. is obtained.

Using in the above described conditions the mixture of diastereoisomers trans- 2-(2-phenylcyclopropyl)-3-carboethoxy-5-carbomethoxy-4-(m-nitrophenyl)-6-methyl-1,4-dihydropyridine, the mixture of diastereoisomers 2-(3-phenyl-3-chloropropyl)-3-carboethoxy-5- carbomethoxy-4-(m-nitrophenyl)-6-methyl-1,4-dihydropyridine. m.p. 110–114° C. is obtained.

Using in the above described conditions the mixtures of diastereoisomers trans-2-(2-phenyl-cyclopropyl)-3,5-dicarboethoxy-4-(m-nitrophenyl)-6-methyl-1,4-dihydropyridine, trans-2-(2-phenylcyclopropyl)-3-carboethoxy-5-carbomethoxy-4-(m-chlorophenyl)-6-methyl-1,4-dihydropyridine, trans-2-(2-phenylcyclopropyl)-3-carboethoxy-5-carbomethoxy-4-(m-trifluoromethylphenyl)-6-methyl-1,4-dihydropyridine and trans-2-(2-phenylcyclopropyl)-3-carboethoxy-5-carboisopropoxy-4-(m-nitrophenyl)-6-methyl-1,4-dihydropyridine the following diastereoisomer mixtures of 2-(3-(chloro-3-phenyl-propyl)-6-methyl-1,4-dihydropyridine were obtained:

3,5-dicarboethoxy-4-(m-nitrophenyl);
3-carboethoxy-5-carbomethoxy-4-(m-chlorophenyl);
3-carboethoxy-5-carbomethoxy-4-(m-trifluoromethylphenyl)
3-carboethoxy-5-carboisopropoxy-4-(m-nitrophenyl).

Using the above described conditions the following compounds were also obtained as diastereoisomers mixtures:

2-(3-chloro-3-phenylpropyl)-3-carboethoxy-5-nitro-4-(m-nitrophenyl)-6-methyl-1,4-dihydropyridine;
2-[3-chloro-3-(pyrid-3-yl)propyl]-3,5-dicarboethoxy-4-(m-methylthiophenyl)-6-methyl-1,4-dihydropyridine;
2-[3-chloro-3-(4-methoxyphenyl)propyl]-3,5-dicarboethoxy-4-(m-methylthiophenyl)-6-methyl-1,4-dihydropyridine;
2-[3-chloro-3-(4-nitrophenyl)propyl]-3,5-dicarboethoxy-4-(m-methylthiophenyl)-6-methyl-1,4-dihydropyridine;
2-[3-chloro-3-(3-thienyl)propyl]-3,5-dicarboethoxy-4-(m -nitrophenyl)-6-methyl-1,4-dihydropyridine.

EXAMPLE 8

A solution of hydrobromic acid in acetic acid (45%; w/v 1.5 ml) is dropped at room temperature to a suspension of the diastereoisomer mixture of trans-2-(2-phenyl-cyclopropyl)-3-carboethoxy-5-carbomethoxy-4-(m-nitrophenyl)-6-methyl-1,4-dihydropyridine (200 mg) in ethanol (2 ml). After 5 minutes the solution is poured in water-ice (20 ml) and it is extracted with ethyl ester (3×20 ml). The organic phase is washed with a NaHCO$_3$ solution (5%, 3×10 ml), dried and concentrated in vacuum.

190 mg of 2-(3-bromo-3-phenylpropyl)-3-carboethoxy-5-carbomethoxy-4-(m-nitrophenyl)-6-methyl-1,4-dihydropyridine are obtained as an amorphous solid.

NMR (CDCl$_3$) δ(TMS): 1.00–1.20 (3H, T); 2.20 (3H,s); 2.20–3.10
(4H,m); 3.70 (3H,s); 3.80–4.10
(2H,q); 4.80–5.00 (3H, s+m); 6.10
(1H broad, s); 7.00–8.10 (9H,m).

EXAMPLE 9

5 ml of a solution of hydrobromic acid in 30% acetic acid are added at 25° C. and under inert atmosphere to a solution of the less polar diastereoisomer of trans-2-(2-phenyl-1-cyclopropyl)-3-carboethoxy-5-cyano-6-methyl-4-(m-nitrophenyl)-1,4-dihydropyridine (0.5 g) in chloroform (5 ml). After 1 1/5 hours the mixture is poured into water (50 ml) and extracted with diethyl ether (25 ml). The phases are separated and the organic one is washed with a 5% NaHCO$_3$ aqueous solution (3×50 ml) and water (2×50 ml), dried on sodium sulphate, filtered and the solvent is evaporated under reduced pressure. 500 mg of the more polar diastereoisomer of 2-(3-phenyl-3-bromopropyl)-3-carboethoxy-5-cyano-6-methyl -4-(m-nitrophenyl)-1,4-dihydropyridine are obtained as an amorphous solid.

NMR (δCDCl$_3$) 7.9–7.2 (m,9H); 6.5 (sb,1H); 5.2 (s,1H);
5.1 (t,1H); 4.1 (q,2H); 3.6 (s,3H); 2.9–1.9 (m,4H); 2.3 (s,3H); 1.2 (t,3H).

Using the conditions of examples 8 and 9, the following compounds were obtained, as diastereoisomeric mixtures:

2-(3-phenyl-3-bromopropyl)-3-carboethoxy-5-nitro-6-methyl-4-(m-nitrophenyl)-1,4-dihydropyridine;
2-(3-phenyl-3-bromopropyl)-3-carboethoxy-5-cyano-6-methyl-4-(m-chlorophenyl)-1,4-dihydropyridine;
2-(3-phenyl-3-bromopropyl)-3-carboethoxy-5-carbonylmethyl-6-methyl-4-(m-nitrophenyl)-1,4-dihydropyridine;

Moreover, using in the same conditions the pure diastereoisomers of trans-2-(2-phenyl-1-cyclopropyl)-3-carboethoxy-6-methyl-5-carbomethoxy-4-(m-chlorophenyl)-1,4-dihydropyridine and trans-2-(2-phenyl-1-cyclopropyl)-3-carboethoxy-5-carbomethoxy-6-methyl-4-(m-methylthiophenyl)-1,4-dihydropyridine, the pure diastereoisomers of:

2-(3-phenyl-3-bromopropyl)-3-carboethoxy-5-carbomethoxy-6-methyl-4-(m-chlorophenyl)-1,4-dihydropyridine;
2-(3-phenyl-3-bromopropyl)-3-carboethoxy-5-carbomethoxy-6-methyl-4-(m-methylthiophenyl)-1,4-dihydropyridine; are obtained.

EXAMPLE 10

0.12 g of sodium azide, 6 mg of tetrabutylammonium bromide, 2 ml of water are added to a solution of the less polar diastereoisomer of 2-(3-phenyl-3-bromopropyl)-3-carboethoxy-5-carbomethoxy-6-methyl-4-(m-nitrophenyl)-1,4-dihydropyridine (0.2 g), in benzene (2 ml), then the biphasic mixture is refluxed for 5 hours, under vigorous stirring.

The mixture is cooled to 25° C., poured into water, extracted with diethylether (20 ml), dried on sodium sulphate, filtered and the solvent is evaporated to dryness under reduced pressure. 180 mg of the less polar diastereoisomer of 2-(3-phenyl-3-azidopropyl)-3-carboethoxy-5-carbomethoxy-6-methyl-5-(m-nitrophenyl)-1,4-dihydropyridine are obtained.

NMR (δCDCl$_3$) 7.9–7.2 (m,9H); 6.5 (s,1H); 5.2 (t+s,2H);
2.8–1.9 (m,4H ; 2.3 (s,3H); 1.2 (t,3H).

In the above indicated conditions, but using the bromopropyl derivatives of example 9, both as pure diastereoisomers and mixtures thereof, the following compounds are obtained:

2-(3-phenyl-3-azidopropyl)-3-carboethoxy-5-cyano-6-methyl-4-(m-nitrophenyl)-1,4-dihydropyridine;
2-(3-phenyl-3-azidopropyl)-3-carboethoxy-5-nitro-6-methyl-4-(m-nitrophenyl)-1,4-dihydropyridine;
2-(3-phenyl-3-azidopropyl)-3-carboethoxy-5-carbomethoxy -6-methyl-4-(m-chlorophenyl)-1,4-dihydropyridine;
2-(3-phenyl-3-azidopropyl)-3-carboethoxy-5-carbomethoxy -6-methyl-4-(m-methylthiophenyl)-1,4-dihydropyridine.

Using in the above indicated conditions instead of sodium azide sodium thiophenoxide, sodium thiomethoxide and potassium thioacetate, the following compounds were also obtained:

2-(3-phenyl-3-phenylthiopropyl)-3,5-dicarboethoxy-4-(m-nitrophenyl)-6-methyl-1,4-dihydropyridine;

2-(3-phenyl-3-methylthiopropyl)-3-carbomethoxy-5-carboethoxy-4-(m-chlorophenyl)-6-methyl-1,4-dihydropyridine;

2-(3-phenyl-3-acetylthiopropyl)-3,5-dicarbomethoxy-4-m-trifluoromethylphenyl)-6-methyl-1,4-dihydropyridine.

EXAMPLE 11

0.2 ml of triethylphosphite are added to a solution of the diastereoisomers mixture 2-(3-phenyl-3-azidopropyl)-3-carboethoxy-5-carbomethoxy-6-methyl-4-(m-nitrophenyl)-1,4-dihydropyridine (0.5 g) in anhydrous benzene (5 ml), and the mixture is stirred for 24 hours at 25° C. under inert atmosphere. 1 ml of an HCl saturated ethanol solution is added thereto and the mixture is stirred at room temperature for other 24 hours.

The mixture is then poured into water-ice, the aqueous phase is alkalinized with 5% NaHCO$_3$ aqueous solution and extracted with diethyl ether (3×50 ml).

The phases are separated, dried on sodium sulphate and filtered. 300 mg of 2-(3-phenyl-3-aminopropyl)-3-carbomethoxy-6-methyl-4-(m-nitrophenyl)-1,4-dihydropyridine, diastereoisomeric mixture, are obtained as an amorphous solid.

NMR (δCDCl$_3$) 7.9–7.2 (m,10H); 6.4 (m,2H); 5.1 (s,1H);
4.8 (m,1H); 4.1 (q,2H); 3.6 (s,3H); 2.9–1.9 (m,4H); 2,3 (s,3H); 1.2 (t,3H).

EXAMPLE 12

120 ml of water are added to a toluene suspension (120 ml) of sodium borohydride (30 g), hexadecyltributylphosphonium bromide (2.27 g) and 15 g of the less polar diastereoisomer of 2-(3-phenyl-3-azidopropyl)-3-carboethoxy-5-carbomethoxy-6 -methyl-4-(m-nitrophenyl)-1,4-dihydropyridine. The mixture is stirred for 24 hours at 70° C., then cooled to room temperature, poured into water (200 ml), extracted with ethylacetate (200 ml), washed with water up to pH 7, dried and evaporated under vacuum. The crude oil (15 g) is purified by chromatography (silice 450 g eluent ethylacetate) to give 7.69 g of the less polar diastereoisomer of 2-(3-phenyl-3-aminopropyl)-3-carboethoxy-5-carbomethoxy-6-methyl-4-(m-nitrophenyl)-1,4-dihydropyridine as a glassy foam. It is dissolved in AcOEt (35 ml) and 1.87 g of maleic acid are added to give 8.2 g of the maleate salt C$_{26}$H$_{29}$O$_6$N$_3$·C$_4$H$_4$O$_4$ (bright yellow crystal): p.f. 149–152° C.

Using the same conditions of the examples 11 and 12 these compound are obtained (diastereoisomeric mixture):

2-(3-phenyl-3-aminopropyl)-3-carboethoxy-5-carbomethoxy -6-methyl-4-(m-methylthiophenyl)-1,4-dihydropyridine;

2-(3-phenyl-3-aminopropyl)-3-carboethoxy-5-carbomethoxy-6-methyl-4-(m-chlorophenyl)-1,4-dihydropyridine;

2-(3-phenyl-3-aminopropyl)-3-carboethoxy-5-carbomethoxy-6-methyl-4-(m-trifluoromethylphenyl)-1,4-dihydropyridine;

2-[3-pyrid-3-yl)-3-aminopropyl]-3,5-dicarboethoxy-6-methyl-4-(m-methylthiophenyl)-1,4-dihydropyridine;

2-[3-(4-methoxyphenyl)-3-aminopropyl]-3,5-dicarboethoxy -6-methyl-4-(m-methylthiophenyl)-1,4-dihydropyridine;

2-[3-(4-nitrophenyl)-3-aminopropyl]-3,5-dicarboethoxy-6 -methyl-4-(m-methylthiophenyl)-1,4-dihydropyridine;

2-[3-(3-thienyl)-3-aminopropyl]-3,5-dicarboethoxy-6-methyl-4-(m-nitrophenyl)-1,4-dihydropyridine.

EXAMPLE 13

0.48 ml of triethylphosphite are added, under inert atmosphere, to a benzene solution (14 ml) of the less polar diastereoisomer of 3-carboethoxy-5-carbomethoxy-6-methyl-4-(m-nitrophenyl)-2-(3-azidopropyl)-1,4-dihydropyridine (1.4 g) and then refluxed for 3 hours.

The mixture is cooled to room temperature and evaporated under vacuum. The crude oil crystallized from diisopropylether (15 ml) to give the less polar diastereoisomer of 3-carboethoxy-5-carbomethoxy-6-methyl-4-(m-nitrophenyl)-2-[3-phenyl-3-diethoxyphosphorylamido-propyl] -1,4-dihydropyridine p.f. 136–139° C. (white powder, 0.95 g).

Using in the above conditions:

2-(3-phenyl-3-azidopropyl)-3-carboethoxy-5-carbomethoxy -4-(m-chlorophenyl)-6-methyl-1,4-dihydropyridine;

2-(3-phenyl-3-azidopropyl)-3-carboethoxy-5-carbomethoxy -4-(m-methylthiophenyl)-6-methyl-1,4-dihydropyridine;

2-(3-phenyl-3-azidopropyl)-3-carboethoxy-5-carbomethoxy -6-methyl-4-(o-trifluoromethylphenyl)-1,4-dihydropyridine;

The following compounds are obtained as diastereoisomer mixtures:

2-(3-phenyl-3-diethoxy-phosphorylamidopropyl)-3-carboethoxy-5-carbomethoxy-6-methyl-4-(m-chlorophenyl)-1,4-dihydropy-ridine;

2-(3-phenyl-3-diethoxy-phosphorylamidopropyl)-3-carboethoxy-5-carbomethoxy-6-methyl-4-(m-methylthiophenyl)-1,4-dihydropyridine;

2-(3-phenyl-3-diethoxy-phosphorylamidopropyl)-3-carboethoxy-5-carbomathoxy-6-methyl-4-(o-trifluoromethylphenyl)-1,4-dihydropyridine.

EXAMPLE 14

0.65 ml of ethyl chlorocarbonate are added to a solution of the less polar diastereoisomer of 2-(3-phenyl-3-aminopropyl)-3-carboethoxy-5-carbomethoxy-6 -methyl-4-(m-nitrophenyl)-1,4-dihydropyridine (200 mg) in anhydrous toluene (2 ml). After two hours at room temperature the mixture is poured into water-ice and alkalinized with a 5% NaHCO$_3$ aqueous solution. It is extracted with diethyl ether (50 ml) and the organic phase is washed with water (2×20 ml), dried on sodium sulphate, filtered and the solvent is evaporated under reduced pressure.

200 mg of the less polar diastereoisomer of 2-[3-phenyl-3-(N-ethoxycarbonylamino)propyl]-3-carboethoxy-5-carbomethoxy-6-methyl-4-(m-nitrophenyl)-1,4-dihydropyridine are obtained as a glassy oil.

NMR (δCDCL$_3$) 8.0–7.2 (m,11H); 5.1 (s,1H); 4.9 (m,1H);
4.2 (q,2H); 4.0 (q,2H); 3.6 (s,3H); 2.9–1.0 (m,4H); 2.3 (s,3H); 1.2 (t,3H); 1.1 (t,3H).

Using in the above conditions the following diastereoisomeric mixtures or pure diastereoisomers of:

2-(3-phenyl-3-aminopropyl)-3-carboethoxy-5-carbomethoxy -6-methyl-4-(m-chlorophenyl)-1,4-dihydropyridine;

2-(3-phenyl-3-aminopropyl)-3-carboethoxy-5-carbomethoxy -6-methyl-4-(o-trifluoromethylphenyl)-1,4-dihydropyridine;
the following compounds are obtained:
2-[3-phenyl-3-(N-ethoxycarbonylamino)propyl]-3-carboethoxy-5-carbomethoxy-6-methyl-4-(m-chlorophenyl)-1,4-dihydropyridine;
2-[3-phenyl-3-(N-ethoxycarbonylamino)propyl]-3-carboethoxy-5-carbomethoxy-6-methyl-4-(o-trifluoromethylphenyl)-1,4-dihydropyridine;
both as pure diastereoisomers or mixtures of diastereoisomers.

EXAMPLE 15

2.4 ml of a solution of 35% NaOH and 10 mg tetrabutylammonium bromide are added to a solution of a diastereoisomeric mixture of 2-(3-phenyl-3-hydroxypropyl)-3-carboethoxy-5-carbomethoxy-6-methyl-(m-nitrophenyl)-1,4-dihydropyridine (200 mg) in ethyl iodide (2 ml). The mixture is stirred at 40° C. for 3 hours, then it is poured into water and ethyl ether (20+20 ml) and the phases are separated. The organic phase is washed with water (2×50 ml), dried on sodium sulphate, filtered and evaporated under reduced pressure. 220 mg of the diastereoisomeric mixture of 2-(3-phenyl-3-ethoxypropyl)-3-carboethoxy-5-carbomethoxy-6-methyl -4-(m-nitrophenyl)-1,4-dihydropyridine, are obtained as a glassy oil.

NMR ($\delta CDCl_3$) 8.0–7.0 (m,10H); 5.1 (sb,1H); 4.3 (t,1H);
4.1 (q,2H); 3.6 (s,3H); 3.3 (q,2H); 2.9–1.9 (m,4H); 2.3 (s,3H); 1.2 (t,3H); 1.1 (t,3H).

In the same conditions, but using the diastereoisomeric mixtures of 2-(3-phenyl-3-hydroxypropyl)-3-carboethoxy-5-carbomethoxy-6-methyl-4-(m-methylthiophenyl)-1,4-dihydropyridine and 2-(3-phenyl-3-hydroxypropyl)-3-carboethoxy-5-carbomethoxy-6-methyl-4-(m-trifluoromethylphenyl)-1,4-dihydropyridine, the following diastereoisomeric mixtures are obtained:
2-(3-phenyl-3-ethoxypropyl)-3-carboethoxy-5-carbomethoxy-6-methyl-4-(m-methylthiophenyl)-1,4-dihydropyridine;
2-(3-phenyl-3-ethoxypropyl)-3-carboethoxy-5-carbomethoxy-6-methyl-4-(m-trifluoromethylphenyl)-1,4-dihydropyridine.

EXAMPLE 16

Acetic anhydride (1 ml) is added to a solution of the polar diastereoisomer of 2-(3-phenyl-3-hydroxypropyl)-3-carboethoxy-5-carbomethoxy-6-methyl-4-(m-nitrophenyl)-1,4-dihydropyridine (1 g) in anhydrous pyridine (2 ml). The mixture is stirred at room temperature for 1 hours, then it is poured into water and ice (20 ml) and extracted with diethyl ether (50 ml).

The organic phase is washed with $H_2SO_4$ (5% aqueous solution) with water (5×40 ml), dried on sodium sulphate, filtered and the solvent is evaporated, thus obtaining 1. g of the most polar diastereoisomer of 2-(3-phenyl-3-acetoxypropyl)-3-carboethoxy-5-carbomethoxy -6-methyl-4-(m-nitrophenyl)-1,4-dihydropyridine as yellow glassy foam.

NMR ($\delta CDCl_3$) 8.0–7.2 m,9H); 6.5 sb,1H); 5.5 (t,1H); 5.2 (sb,1H); 4.2 (q,2H); 3.5 (s,3H); 1.9–2.7 (m,4H); 2.2 (s,3H); 2.0 (s,3H); 1.2 (t,3H).

In the above conditions, but using 2-(3-hydroxypropyl)- and 2-(3-aminopropyl)-1,4-dihydropyridine, the following -6-methyl-1,4-dihydropyridines are obtained:

2-(3-acetoxy-3-phenylpropyl)-3,5-dicarboethoxy-4-(m-methylthiophenyl);
2-(3-acetoxy-3-phenylpropyl)-3,5-dicarboethoxy-4-(2-fluoro-5-methylthiophenyl);
2-(3-acetoxy-3-phenylpropyl)-3-carboethoxy-5-carboisopropoxy-4-(p-fluorophenyl);
2-(3-acetoxy-3-phenylpropyl)-3-carboethoxy-5-cyano-4-(m-nitrophenyl);
2-(3-acetoxy-3-phenylpropyl)-3,5-dicarboethoxy-4-(m-methylthiophenyl);
2-(3-acetoxy-3-phenylpropyl)-3,5-dicarboethoxy-4-(2-nitro-5-methylthiophenyl);
2-[3-acetoxy-3-(pyrid-3-yl)propyl]-3,5-dicarboethoxy-4-(m-methylthiophenyl);
2-[3-acetoxy-3-(4-nitrophenyl)propyl]-3,5-dicarboethoxy-4-(m-methylthiophenyl);
2-[3-acetoxy-3-(2-thienyl)propyl]-3-carboethoxy-5-carbomethoxy-4-(m-nitrophenyl);
2-[3-acetoxy-3-(4-bromophenyl)propyl]-3-carboethoxy-4-(m-nitrophenyl);
2-[3-acetamido-3-phenylpropyl]-3-carboethoxy-5-carboethoxy-4-(o-methylthiophenyl);
2-[3-acetamido-3-phenylpropyl]-3,5-dicarboethoxy-4-(m-methylthiophenyl);
2-[3-acetamido-3-(2-thienyl)propyl]-3-carboethoxy-5-carbomethoxy-4-(m-nitrophenyl);
2-[3-acetamido-3-(4-methoxyphenyl)propyl]-3,5-dicarboethoxy-4-(m-methylthiophenyl).

EXAMPLE 17

A solution of 2-(3-hydroxy-3-phenyl)propyl-3-carboethoxy-5-carbomethoxy-4-(m-nitrophenyl)-6-methyl-1,4-dihydropyridine (2.0 g), p-nitrobenzoylchloride (0.85 g) and triethylamine (0.64 g) in methylene chloride (20 ml) is stirred at room temperature for 24 hours. p-nitrobenzoylchloride (0.3 g) and triethylamine (0.20 ml) are then added, and stirring is continued for 72 hours; the mixture is finally evaporated under vacuum and diluted with ethyl ether (50 ml). The organic mixture is washed with water (3×10 ml), NaOH (1N, 2×5 ml), water (5×10 ml), dried ($Na_2SO_4$) and concentrated and vacuum to give 2-[3-(p-nitrobenzoyloxy)-3-phenylpropyl]-3-carboethoxy-5-carbomethoxy-4-(m-nitrophenyl)-6-methyl-1,4-dihydropyridine (2.15 g). Glassy solid, m.p. 75–90° C.

In the same way but using benzoylchloride and pivaloylchloride instead of p-nitrobenzoylchloride, the following derivatives are obtained:
2-(3-t-butylcarbonyloxy-3-phenylpropyl)-3-carboethoxy-5 -carbomethoxy-4-(m-nitrophenyl)-6-methyl-1,4-dihydropyridine;
2-3-phenylpropyl)-3-carboethoxy-5-carbomethoxy-4-(m-nitrophenyl)-6-methyl-1,4-dihydropyridine;
2-(3-benzoyloxy-3-phenylpropyl)-3-carboethoxy-5-carbomethoxy-4-(m-nitrophenyl)-6-methyl-1,4-dihydropyridine.

EXAMPLE 18

A solution of diastereoisomers of 2-(3-phenyl-3-hydroxypropyl)-3-carboethoxy-5-carbomethoxy -4-(m-nitrophenyl)-6-methyl-1,4-dihydropyridine (100 mg) in formic acid (2 ml) is stirred for 24 hours at room temperature, then it is diluted with water (10 ml) and extracted with ethyl ether (15 ml); the organic phase is washed with a NaHCO solution (5%, 3×5 ml , water (3×5 ml), dried ($Na_2SO_4$) and concentrated under vacuum to give 2-(3-formyloxy-3-phenylpropyl)-3-carboethoxy-5-carbomethoxy-4-(m-nitrophenyl)-6-methyl-1,4- dihydropyridine, diastereoisomer mixture identical to the compound obtained in example 1.

EXAMPLE 19

A solution of the diastereoisomeric mixture of 2-(3-phenyl-3-bromopropyl)-3-carboethoxy-5-carbomethoxy-6 -methyl-4-(m-nitrophenyl)-1,4-dihydropyridine (1 g) in anhydrous THF (10 ml) is added under $N_2$ at room temperature to a suspension of $LiAlH_4$ (120 mg, powder) in anhydrous THF (ml 2).

The mixture is heated at reflux temperature for 6 hours, then it is cooled at 0° C. and poured under vigorous stirring into $H_2O$ and ice (100 ml), acidified to pH 3–4 with a 1N HCl solution and extracted with diethyl ether (2×50 ml . The collected organic phases are washed to neutrality with a 5% $NaHCO_3$ aqueous solution, water (3×50 ml), dried on sodium sulphate, filtered and the solvent is evaporated under reduced pressure. A yellow oil is obtained (0.85 g) that is purified on chromatographic column (silica 50 g, eluent isopropyl ether:hexane 3:7), to give 0.22 g of 2-(3-phenylpropyl)-3-carboethoxy-5-carbomethoxy-6-methyl-4-(m-nitrophenyl)-1,4-dihydropyridine, as a yellow oil that crystallizes spontaneously from isopropyl ether, and is recrystallized from ethanol, m.p. 125–127° C.

In the same conditions but using bromoderivatives such as:

2-(3-phenyl-3-bromopropyl)-3-carboethoxy-5-carbomethoxy -6-methyl-4-(m-chlorophenyl)-1,4-dihydropyridine;

2-(3-phenyl-3-bromopropyl)-3-carboethoxy-5-carbomethoxy -6-methyl-4-(o-trifluoromethylphenyl)-1,4-dihydropyridine;

2-(3-phenyl-3-bromopropyl)-3-carboethoxy-5-carboisopropoxy-6-methyl-4-(m-methylthiophenyl)-1,4-dihydropyridine;

the following compounds are obtained:

2-(3-phenylpropyl)-3-carboethoxy-5-carbomethoxy-6-methyl-4-(m-chlorophenyl)-1,4-dihydropyridine;

2-(3-phenylpropyl)-3-carboethoxy-5-carbomethoxy-6-methyl-4-(o-trifluoromethylphenyl)-1,4-dihydropyridine;

2-(3-phenylpropyl)-3-carboethoxy-5-carboisopropoxy-6-methyl-4-(m-methylthiophenyl)-1,4-dihydropyridine.

EXAMPLE 20

A solution of formyl acetic anhydride (15 ml), prepared heating at 60° C. for one hour a mixture of formic acid (5 ml) and acetic anhydride (10 ml), is dropped into a solution of 2-(3-amino-3-phenylpropyl)-3-carboethoxy-5-carbomathoxy-4-(m-nitrophenyl)-6-methyl-1,4-dihydropyridine (3.5 g) in anhydrous 1,2-dimethoxyethane (35 ml) under $N_2$ atmosphere at 0° C. The mixture is stirred at room temperature for 4 hours, then it is poured into water-ice (250 ml) and extracted with ethyl acetate (3×50 ml). The organic phase is washed with a saturated $NaHCO_3$ solution (3×30 ml) water (3×30 ml), dried ($Na_2SO_4$) and evaporated. The residue is purified by chromatography on silica gel (90 g, eluent hexane/ethyl acetate 50/50) to give 2.8 g of 2-(3-phenyl-3-formylaminopropyl)-3-carboethoxy-5-carbomethoxy-4-(m-nitrophenyl) 6-methyl-1,4-dihydropyridine (diastereoisomeric mixture). Yellow foam.

NMR ($\delta CDCl_3$) 8.20–6.70 (m,12H); 5.10 (m,2H); 4.1 (q,2H);

3.6 (s,3H);; 2.8–1,9 (m,4H); 2.3 (s,3H); 1.2 (t,3H).

In the same way the following compounds were prepared:

2-(3-phenyl-3-formylaminopropyl)-3-carboethoxy-5-carbomethoxy-4-(m-chlorophenyl)-6-methyl-1,4-dihydropyridine;

2-(3-phenyl-3-formylaminopropyl)-3-carboethoxy-5-carbomethoxy-4-(m-methylthiophenyl)-6-methyl-1,4-dihydropyridine.

EXAMPLE 21

In a polyethylene flask, a mixture of trans-2-(2-phenylcyclopropyl)-3-carboethoxy-5-carbomethoxy-4-(m-nitrophenyl)-6-methyl-1,4-dihydropyridine (1 g) and KF (0.4 g), suspended in the HF/pyridine complex (10 ml), is stirred under $N_2$ atmosphere at 0° C. for 2 hours, then at room temperature for 24 hours. It is finally poured into a KF saturated water solution (80 ml) and extracted with ethyl ether. The organic phase is washed with a saturated $NaHCO_3$ solution (3×50 ml), water (3×30 ml), dried ($Na_2SO_4$) and evaporated under vacuum.

The residue is purified by chromatography on silica gel (70 g; eluent isopropyl ether/hexane 90/10).

In this way, 0.2 g of 2-(3-fluoro-3-phenylpropyl)-3-carboethoxy-5-carbomethoxy-4-(m-nitrophenyl)-6-methyl-1,4-dihydropyridine (diastereoisomers mixture) are obtained as an amorphous solid.

NMR ($\delta CDCl_3$) 8.10–7.00 (m,9H); 6.10 (sb,1H); 5.00 s,1H); 4.90 (m,1H); 4.10–3.80 (q,2H);

3.70 (s,3H); 3.0–2.2 (m,4H); 2.20 (s,3H); 1.2–1.10 (t,3H).

In the same conditions of example 21, but using the more polar diastereoisomer trans-2-(phenylcyclopropyl)-3-carboethoxy-5-carbomethoxy-4-(m-nitrophenyl)-6-methyl-1,4-dihydropyridine, the less polar diastereoisomer 2-(3-fluoro-3-phenylpropyl)-3-carboethoxy-5-carbomethoxy-4-(m-nitrophenyl)-6-methyl-1,4-dihydropyridine is obtained and using the less polar diastereoisomer trans-2-(2-phenyl-cyclopropyl)-3-carboethoxy-5-carbomethoxy-4-(m-nitrophenyl)-6-methyl-1,4-dihydropyridine, the more polar diastereoisomer 2-(3-fluoro-3-phenylpropyl)-3-carboethoxy-5-carbomethoxy-4-(m-nitrophenyl) -6-methyl-1,4-dihydropyridine is obtained.

In the same conditions of example 21, the following compounds were obtained:

2-(3-fluoro-3-phenylpropyl)-3-carboethoxy-5-carbomethoxy-4-(m-methylthiophenyl)-6-methyl-1,4-dihydropyridine;

2-(3-fluoro-3-phenylpropyl)-3-carboethoxy-5-carbomethoxy-4-(m-chlorophenyl)-6-methyl-1,4-dihydropyridine;

2-(3-fluoro-3-phenylpropyl)-3,5-dicarboethoxy-4-(m-nitrophenyl)-6-methyl-1,4-dihydropyridine;

EXAMPLE 22

A solution in anhydrous THF (10 ml) of the diastereoisomeric mixture of 2-(3-bromo-3-phenyl-propyl)-3-carboethoxy-5-carbomethoxy-6-methyl-4-(m-nitrophenyl)-1,4-dihydropyridine (1 g) is added to anhydrous tetrabutylammonium fluoride (0.5 g) in anhydrous THF and stirred for 5 hours. The mixture is then poured into water (50 ml) and extracted with ethylacetate (20 ml×2). The organic phase is then washed with water, dried with $Na_2SO_4$ and evaporated to dryness to give 0.9 g of a crude yellow oil, which is purified by cromatography (silica g 30/eluent diisopropyl ether/hexane 90/10) to give 0.08 g of a diastereoisomeric mixture of 2-(3-phenyl)-3-fluoropropyl)-3-carboethoxy-
— -carbomethoxy-6-methyl-4-(m-nitrophenyl)-1,4-
dihydropyridine as a yellow foam identical to the sample obtained in the example 21.

We claim:

1. A compound of formula I

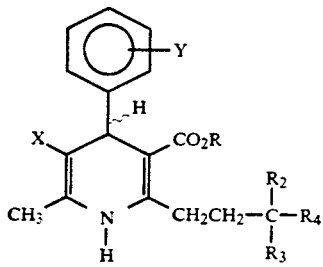

wherein:

X is a $-CO_2R_1$, cyano, nitro, $-COCH_3$ group;

each of R and $R_1$, which may be the same or different, is a primary, secondary or tertiary, saturated or unsaturated, linear or branched $C_1-C_6$ alkyl group which is unsubstituted or substituted by one or more hydroxy, $C_1-C_7$-monoalkylamino, di-$C_1-C_7$-alkylamino, benzylamino, $C_1-C_6$-alkoxy, phenoxy groups optionally substituted by one or more $C_1-C_6$ alkyl, $C_1-C_6$ alkoxy, halo-$C_1-C_6$ alkyl, halo-$C_1-C_6$ alkoxy, halogen, nitro, cyano, $C_1-C_6$ alkoxycarbonyl, $C_1-C_6$ alkylthio, $NHCOR_5$, $SO_2R_6$, $C_1-C_4$-alkylamino, di($C_1-C_4$)alkylamino, hydroxy;

$R_2$ is hydrogen;

$R_3$ is a hydroxy, $-OCOR_5$, $OSO_2R_6$, azide, amino, $-NHPO(OR_7)_2$, $-NHCOR_5$ group, a $C_1-C_4$-alkoxy group or a fluorine, chlorine, bromine or iodine atom, a SH group, a $SCOR_6$ or a $C_1-C_6$-alkylthio, phenylthio or benzylthio group;

$R_4$ is an optionally substituted aromatic or an optionally substituted 5- or 6-membered heteroaromatic group selected from the group consisting of, pyridyl, pyrrolyl, pyrimidyl, pyridazyl, oxazolyl, isooxazolyl, thiazolyl, triazolyl, pyrazinyl, thiazinyl, quinolyl, iooquinolyl, benzothienyl, quinazolyl, indolyl, benzofuranyl, indazolyl, benzooxazolyl, and benzothiazolyl, wherein the substituent is selected from one or more hydroxy, $C_1-C_7$-monoalkylamino, di-$C_1-C_7$-alkylamino, benzylamino, $C_1-C_6$-alkoxy, phenoxy groups optionally substituted by one or more $C_1-C_6$ alkyl, $C_1-C_6$ alkoxy, halo-$C_1-C_6$ alkyl, halo-$C_1-C_6$-alkoxy, halogen, nitro, cyano, $C_1-C_6$ (alkoxycarbonyl, $C_1-C_6$ alkylthio, $NHCOR_5$, $SO_2R_6$, $C_1-C_4$-alkylamino, di($C_1-C_4$)alkylamino, hydroxy;

Y is one or more substituents, that can be the same or different, selected from the group consisting of $C_1-C_4$-alkoxy, halogen, nitro, cyano, $C_1-C_6$-alkoxycarbonyl, $C_1-C_6$-alkylthio, halo-$C_1-C_6$-alkyl, halo-$C_1-C_6$-alkoxy, $NHCOR_5$ and $NHSO_2R_6$;

$R_5$ is hydrogen or a $C_1-C_4$-alkyl, a trihalomethyl, $C_1-C_4$-alkoxy or phenyl group, optionally substituted by one or more nitro, halogen, $C_1-C_4$ alkyl, $C_1-C_4$-alkoxy, amino groups;

$R_6$ is hydrogen or a $C_1-C_4$-alkyl, trihalomethyl, phenyl or p-methylphenyl group;

$R_7$ is a $C_1-C_4$-alkyl group or a phenyl group; an enantiomer, diastereoisomer or salt thereof wit a pharmaceutically acceptable acid or base.

2. A compound according to claim 1 wherein:

X is carbomethoxy, carboethoxy, carboisopropoxy, cyano or nitro;

R is ethyl;

$R_3$ is OH, $-OCOR_5$, $OSO_2R_6$, azido, amino, $-NHCOR_5$, ethoxy, fluorine, bromine or chlorine;

$R_4$ is phenyl;

Y is nitro, chloro, trifluoromethyl or methylthio;

$R_5$ is hydrogen, trifluoromethyl or ethoxy;

$R_6$ is methyl.

3. A compound according to claim 1, selected from the group consisting of:

2-(3-formyloxy-3-phenylpropyl)-3-carboethoxy-5-carbomethoxy-4-(m-nitrophenyl)-6-methyl-1,4-dihydropyridine;

2-(3-formyloxy-3-phenylpropyl)-3-carboethoxy-5-carbomethoxy-4-(m-chlorophenyl)-6-methyl-1,4-dihydropyridine;

2-(3-formyloxy-3-phenylpropyl)-3-carboethoxy-5-carbomethoxy-4-(m-trifluoromethylphenyl)-6-methyl-1,4-dihydropyridine;

2-(3-trifluoroacetoxy-3-phenylpropyl)-3-carboethoxy-5-carbomethoxy-4-(m-nitrophenyl)-6-methyl-1,4-dihydropyridine;

2-(3-azido-3-phenylpropyl)-3-carboethoxy-5-carbomethoxy -4-(m-nitrophenyl)-6-methyl-1,4-dihydropyridine;

2-(3-phenyl-3-hydroxypropyl)-3-carboethoxy-5-carbomethoxy-4-(m-nitrophenyl)-6-methyl-1,4-dihydropyridine;

2-(3-phenyl-3-pydroxypropyl)-3,5-dicarboethoxy-4-(m-methylthiophenyl)-6-methyl-1,4-dihydropyridine;

2-(3-phenyl-3-hydroxypropyl)-3-carboethoxy-5-carbomethoxy-4-(m-trifluoromethylphenyl)-6-methyl-1,4-dihydropyridine;

2-(3-phenyl-3-hydroxypropyl)-3,5-dicarboethoxy-4-(m-chlorophenyl)-6-methyl-1,4-dihydropyridine;

2-(3-phenyl-3-bromopropyl)-3-carboethoxy-5-cyano-4-(m-nitrophenyl)-6-methyl-1,4-dihydropyridine;

2-(3-phenyl-3-bromopropyl)-3-carboethoxy-5-nitro-4-(m-nitrophenyl)-6-methyl-1,4-dihydropyridine;

2-(3-fluoro-3-phenylpropyl)-3-carboethoxy-5-cyano-4-(m-nitrophenyl)-6-methyl-1,4-dihydropyridine;

2-(3-azido-3-phenylpropyl)-3-carboethoxy-5-nitro-4-(m-nitrophenyl)-6-methyl-1,4-dihydropyridine;

2-(3-azido-3-phenylpropyl)-3-carboethoxy-5-carboisopropoxy-4-(m-nitrophenyl)-6-methyl-1,4-dihydropyridine;

2-(3-azido-3-phenylpropyl)-3-carboethoxy-5-carboethoxy-4-(m-chlorophenyl)-6-methyl-1,4-dihydropyridine;

2-(3-azido-3-phenylpropyl)-3-carboethoxy-5-carboethoxy-4-(m-methylthiophenyl)-6-methyl-1,4-dihydropyridine; p0 2-(3-phenyl-3-aminopropyl)-3-carboethoxy-5-carbomethoxy -4-(m-nitrophenyl)-6-methyl-1,4-dihydropyridine;

2-(3-phenyl-3-aminopropyl)-3-carboethoxy-5-carbomethoxy -4-(m-chlorophenyl)-6-methyl-1,4-dihydropyridine;

2-(3-phenyl-3-aminopropyl)-3-carboethoxy-5-carbomethoxy -4-(m-methylthiophenyl)-6-methyl-1,4-dihydropyridine;

2-(3-phenyl-3-aminopropyl)-3-carboethoxy-5-carbomethoxy -4-(m-trifluoromethylphenyl)-6-methyl-1,4-dihydropyridine;

2-[3-phenyl-3-(N-ethoxycarbonyl)aminopropyl]-3-carboethoxy-5-carbomethoxy-4-(m-nitrophenyl)-6-methyl-1,4-dihydropyridine;

2-(3-phenyl-3-formylaminopropyl)-3-carboethoxy-5-carbomethoxy-4-(m-nitrophenyl)-6-methyl-1,4-dihydropyridine;

2-(3-phenyl-3-formylaminopropyl)-3-carboethoxy-5-carbomethoxy-4-(m-chlorophenyl)-6-methyl-1,4-dihydropyridine 2-(3-phenyl-3-formylaminopropyl)-3-carboethoxy-5-carbomethoxy-4-(m-methylthiophenyl)-6-methyl-1,4-dihydropyridine;

2-(3-ethoxy-3-phenylpropyl)-3-carboethoxy-5-carbomethoxy--4-(m-nitrophenyl)-6-methyl-1,4-dihydropyridine;

2-(3-methylsulfonyloxy-3-phenyl)propyl-3-carboethoxy-5-carbomethoxy-4-(m-nitrophenyl)-6-methyl-1,4-dihydropyridine;

2-(3-azido-3-phenylpropyl)-3-carboethoxy-5-cyano-4-(m-nitrophenyl)-6-methyl-1,4-dihydropyridine;

2-(3-chloro-3-phenylpropyl)-3,5-dicarboethoxy-4-(m-nitrophenyl)-6-methyl-1,4-dihydropyridine;

2-(3-chloro-3-phenylpropyl)-3-carboethoxy-5-carbomethoxy-4-(m-chlorophenyl)-6-methyl-1,4-dihydropyridine;

2-(3-chloro-3-phenylpropyl)-3-carboethoxy-5-carbomethoxy-4-(m-trifluoromethylphenyl)-6-methyl-1,4-dihydropyridine;

2-(3-chloro-3-phenylpropyl)-3-carboethoxy-5-carbomethoxy-4-(m-nitrophenyl)-6-methyl-1,4-dihydropyridine;

2-(3-chloro-3-phenylpropyl)-3-carboethoxy-5-carboisopropoxy-6-methyl-4-(m-nitrophenyl)-1,4-dihydropyridine;

2-(3-bromo-3-phenylpropyl)-3-carboethoxy-5-carbomethoxy -4-(m-nitrophenyl)-6-methyl-1,4-dihydropyridine;

2-(3-bromo-3-phenylpropyl)-3-carboethoxy-5-carbomethoxy -4-(m-chlorophenyl)-6-methyl-1,4-dihydropyridine;

2-(3-fluoro-3-phenylpropyl)-3-carboethoxy-5-carbomethoxy-4-(m-nitrophenyl)-6-methyl-1,4-dihydropyridine;

2-(3-fluoro-3-phenylpropyl)-3-carboethoxy-5-carbomethoxy-4-(m-methylthiophenyl)-6-methyl-1,4-dihydropyridine;

2-[3-formyloxy-3-(pyrid-3-yl)propyl]-3,5-dicarboethoxy-4-(m-methylthiophenyl)-6-methyl-1,4-dihydropyridine;

2-[3-formyloxy-3-(4-methoxyphenyl)propyl]-3,5-dicarboethoxy-4-(m-methylthiophenyl)-6-methyl-1,4-dihydropyridine;

2-[3-hydroxy-3-(4-nitrophenyl)propyl]-3,5-dicarboethoxy -4-(m-methylthiophenyl)-6-methyl-1,4-dihydropyridine;

2-[3-chloro-3-(4-methoxyphenyl)propyl]-3,5-dicarboethoxy-4-(m-methylthiophenyl)-6-methyl-1,4-dihydropyridine;

2-[3-(4-methoxyphenyl)-3-aminopropyl]-3,5-dicarboethoxy -6-methyl-4-(m-methylthiophenyl)-1,4-dihydropyridine;

2-[3-(pyrid-3-yl)-3-aminopropyl]-3,5-dicarboethoxy-6-methyl-4-(m-methylthiophenyl)-1,4-dihydropyridine;

2-[3-acetamido-3-(4-methoxyphenyl)propyl]-3,5-dicarboethoxy-4-(m-methylthiophenyl)-6-methyl-1,4-dihydropyridine;

2-(3-phenyl-3-phenylthiopropyl)-3,5-dicarboethoxy-4-(m-nitrophenyl)-6-methyl-1,4-dihydropyridine;

2-(3-phenyl-3-methylthiopropyl)-3-carbomethoxy-5-carboethoxy-4-(m-chlorophenyl)-6-methyl-1,4-dihydropyridine;

2-(3-phenyl-3-acetylthiopropyl)-3,5-dicarbomethoxy-(m-trifluoromethylphenyl)-6-methyl-1,4-dihydropyridine;

an enantiomer, diastereoisomer or salt thereof with a pharmaceutically acceptable acid or base.

4. A pharmaceutical composition containing as an active ingredient a compound according to any one of claims 1, 2 or 3 in admixture with a pharmaceutically acceptable vehicle.

5. A method of treating hypertension which comprises administering to a patient suffering from hypertension an anti-hypertension effective amount of a compound according to any one of claims 1, 2 or 3.

* * * * *